United States Patent [19]

Loughman et al.

[11] 4,365,633
[45] Dec. 28, 1982

[54] PATIENT-OPERATED PACEMAKER PROGRAMMER

[75] Inventors: James Loughman, Randwick; Christopher N. Daly, Bilgola Plateau; Ronald A. C. Washington, Seaforth, all of Australia

[73] Assignee: Telectronics Pty. Ltd., Lane Cove, Australia

[21] Appl. No.: 123,916

[22] Filed: Feb. 22, 1980

[51] Int. Cl.³ .............................................. A61N 1/36
[52] U.S. Cl. .............................................. 128/419 PG
[58] Field of Search ................. 128/419 PG, 419 DT, 128/419 R, 421, 422

[56] References Cited

U.S. PATENT DOCUMENTS

| | | | |
|---|---|---|---|
| 2,771,554 | 11/1956 | Gratzl | 128/421 |
| 3,198,195 | 8/1965 | Chardack | 128/419 PG |
| 3,311,111 | 3/1967 | Bowers | 128/419 PG |
| 3,518,997 | 7/1970 | Sessions | 128/419 PG |
| 4,049,004 | 9/1977 | Walters | 128/419 PG |

*Primary Examiner*—William E. Kamm
*Attorney, Agent, or Firm*—Gottlieb, Rackman & Reisman

[57] ABSTRACT

There is disclosed a pacemaker programmer for operation by a patient. The programmer can be pre-set by the physician to allow the patient to set his pacemaker in any one of a limited number of states, the states controllable by the patient being a sub-set of the set controllable by the physician with use of his conventional-type programmer. In the illustrative embodiment of the invention, while the physician programmer can control eight different rates, the patient programmer can set only three of these ("exercise", "awake" and "sleep" values), the particular values being preselected by the physician.

23 Claims, 13 Drawing Figures

| | RATE |
|---|---|
| | 60 |
| | 75 |
| | 65 |
| | 70 |
| | 80 |
| NOT USED WITH SYNCHRONOUS MODE | 110 |
| | 90 |
| | 100 |

| | MODE/LEVEL |
|---|---|
| VENTRICULAR INHIBITED | HI |
| | HI |
| | LO |
| | LO |
| ASYNCHRONOUS | HI |
| | LO |
| SYNCHRONOUS | HI |
| | LO |

PATIENT-OPERATED PACEMAKER PROGRAMMER

This invention relates to pacemaker programmers, and more particularly to a pacemaker programmer which can be operated by a patient.

A typical present-day programmable cardiac pacemaker can be programmed by a physician to assume any one of a number of states. Toward this end, the physician utilizes a pacemaker programmer which transmits electromagnetic energy in the form of coded pulses through the patient's body, pacemaker detecting circuitry responding to these pulses and setting the pacemaker state in accordance with the transmitted code. Several different functions usually can be controlled.

For example, a typical pacemaker marketed by the assignee of this application can be programmed to pace at any one of eight different rates (60, 65, 70, 75, 80, 85, 90, 100 and 110 pulses per minute). The pacemaker can also be set to generate pulses at either a high or a low level (5.2 or 2.6 volts). Lastly, the pacemaker can be set to operate in any one of three modes. In the ventricular-inhibited mode (also known as "demand" operation), a pacemaker pulse is generated only when the heart fails to beat spontaneously within a predetermined time interval subsequent to the last beat. In the synchronous mode, the pacemaker operates in the same way to generate a stimulating pulse whenever the heart fails to beat, but a pulse is also generated whenever the heart does beat spontaneously, the pacemaker pulse thus "reinforcing" the spontaneous beat. In the asynchronous mode, the pacemaker beats at a fixed rate independent of spontaneous heart activity.

With eight possible rates, two possible pulse levels and three possible modes, it is apparent that theoretically the pacemaker can be operated in any one of forty-eight different states. The physician programmer is capable of controlling any one of these states. (As will become apparent below, some combinations of mode and rate are not allowed, so there are actually fewer than forty-eight states). Over extended periods of time, it may be necessary for the physician to change the value of one, two or even all three of the rate, mode and level parameters which characterize pacemaker operation. (As used herein, even mode is considered a pacemaker "parameter" and the mode setting is considered a "value".)

But it may be desireable for the patient to have his pacemaker state changed more often. For example, the physician might feel that different rates are advisable when the patient is sleeping and when he is awake. Even when he is awake, it might be preferred to have two different rates depending upon whether the patient is exercising or not. It is not feasible, of course, to have the patient visit his doctor several times a day in order to have the state of his pacemaker changed.

It is just as impractical, and probably dangerous, to provide the patient with a programmer of the type used by the physician. Present-day programmers are too complex for patient use, and they require the exercise of clinical judgment. Moreover, if the patient sets the programmer erroneously, the mistake could be fatal.

It is a general object of our invention to provide a pacemaker programmer which can be operated by a patient to control his pacemaker to meet varying requirements, but without requiring the patient to make clinical decisions or allowing him to make critical mistakes.

In accordance with the principles of our invention, the patient is given a programmer which can control state selection from only a limited number of states; these states comprise a sub-set of the set under control of the physician. The patient programmer may be designed to change the values of less than all of the parameters under control of the physician. For example, in the illustrative example of the invention, the patient programmer cannot control a change in the mode of operation or the pulse level; only the pacemaker rate can be changed. Furthermore, rather than to allow the patient to select from all of the values associated with a parameter under his control, he may be limited to only a sub-set of them. In the illustrative embodiment of the invention, the patient programmer can select from only three of the eight rate values under control of the physician.

Whether the patient programmer is limited in the number of parameters which can be changed, or the number of values associated with any particular parameter, or both, the net result is the same—the patient can control his pacemaker to change to a state selected from only a sub-set of the set of states under control of the physician. (While present-day programmable pacemakers and programmers operate with discrete parameter values, the principles of our invention are equally applicable to systems in which parameter values can be adjusted over continuous ranges.) In a sense, our invention is not just a programmer which can control a number of states less than the number under control of the physician programmer. What is really involved is a system which includes not only the patient programmer, but also the pacemaker itself and the physician programmer. To a conventional "set" of a pacemaker and a physician programmer, we add a patient programmer which is characterized by being capable of controlling a plurality of states which is a sub-set of those which characterize the pacemaker and the physician programmer.

But there are two practical problems in implementing such a system. The first pertains to the number of patient-operated programmers which might have to be made available. Consider a pacemaker which can assume any one of forty-eight possible states. Suppose that the patient programmer is to control changes among only three states. Since there are 17,296 different combinations of three states from a total of forty-eight, it is apparent that for maximum flexibility (while at the same time limiting patient state selection), an inordinate number of patient programmers would have to be kept in stock. Even if it is assumed that only the rate parameter will be under control of the patient, that is, he will be allowed to select from only three of the eight possible rates under control of the physician, since any given patient may require a different sub-set of three rates, there is still a substantial problem in stocking patient programmers. There are 56 different combinations of three rates from a total of eight, and it is just not practical to stock so many different types of patient programmers.

The other practical problem is that most patients just cannot be relied upon to select correct values of mode, rate and pulse level depending upon momentary requirements, even if the choice is limited. For example, if the patient programmer can select from only three rates, e.g., 65, 75 and 90 pulses per minute, it would be dangerous to expect the patient to remember that it is the highest rate which should be selected for exercise. In a moment of confusion, prior to exercise the patient might actually select the slowest pacing rate.

In the illustrative embodiment of our invention, in which the patient programmer cannot control a change in pulse level or mode, and can permit a selection from among only three of eight possible rates, there is no need to stock 56 different patient programmers. Only one is required. The unit includes switches which can be set by the physician to select the three rates which will be under patient control. These switches are internal to the unit and a cover plate must be unscrewed in order to obtain access to them. There is thus little danger that the patient will control any pacing rate other than the three pre-selected by the physician (unless he deliberately unscrews the cover plate and changes the switch settings, against orders).

This is not to say that the manufacturer should never provide pre-wired patient programmers. In those cases where a particular sub-set of states is to be pre-selected for a large number of patients, it may be desirable to provide a "fixed" patient programmer, with a "physician programmable" patient programmer being provided for the more unusual cases.

The patient programmer includes a slide switch which allows the patient to select one of the three rates pre-selected by the physician. But the actual rate values are not labeled on the unit. Instead, the labels associated with the slide switch represent day-to-day physiological requirements. In lieu of labeling the three positions of the switch 65, 75 and 90 pulses per minute (or any other values pre-selected by the physician), the indicia may be "sleep", "awake" and "exercise". This has two main advantages. First, there is no need to provide different numerical indicia depending upon the three rate values pre-selected by the physician. Second, and more important, while the patient may get confused as to which rate applies to which function, he certainly cannot be confused by the three words; he knows whether he is going to sleep, whether he has just awakened, or whether he is about to begin exercising.

In other respects, the patient programmer is similar to the conventional physician programmer, although some options may be omitted (e.g., physician programmers can often actually monitor the pacemaker rate, but this feature is not included in the patient programmer of the illustrative embodiment of the invention.) The patient programmer operates in the same range as the physician programmer, up to 30 mm from the pacemaker. It is powered by re-chargeable batteries, and code transmission is inhibited if the battery charge is depleted. Auditory and visual signals are provided to indicate whether code transmission has taken place.

Further objects, features and advantages of our invention will become apparent upon consideration of the following detailed description in conjunction with the drawing, in which:

FIGS. 9-11 are a schematic of the circuit of the patient programmer, with FIG. 12 illustrating the arrangement of the three figures.

Figure 1:
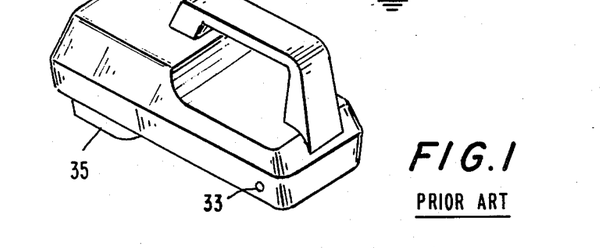
FIG. 1 depicts the overall configuration of a typical prior art physician programmer.

A conventional physician programmer is shown in FIG. 1. The actual circuitry of the physician programmer need not be understood for an understanding of the present invention. Rather, it is only necessary to understand what it is that the physician programmer controls. Physician programmers per se are well known in the art.

When used, the physician holds the programmer with protrusion 35, the coil pod, on the patient's chest over the pacemaker. When a button (not shown on either FIGS. 1 or 2) is pressed, a series of current pulses flow through the coil and generate a pulsating electromagnetic field. This field pulses a relay in the pacemaker, to be described below. On FIG. 1 there can also be seen a jack for connecting a charging circuit, in order to re-charge the internal batteries.

Figure 2:
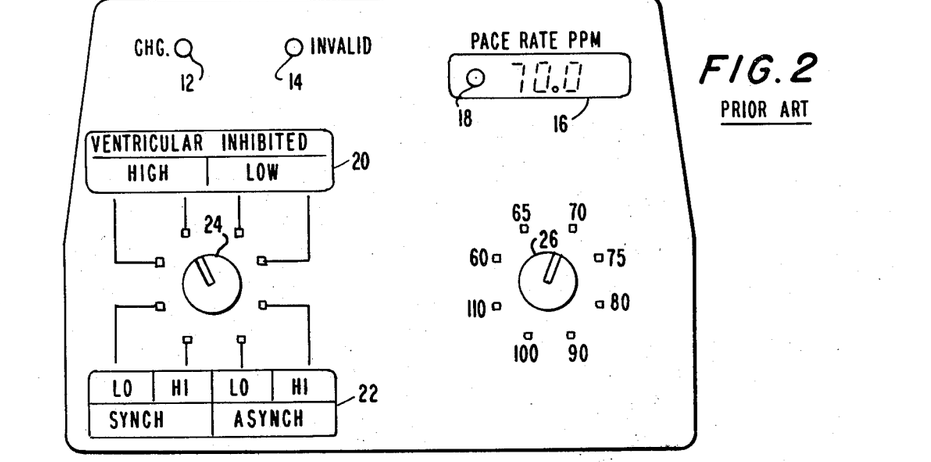
FIG. 2 depicts the type of control panel to be found on a prior art physician programmer (similar to but not exactly that of the Telectronics 173 Programmer)

FIG. 2 depicts the face of the physician programmer. Rate switch 26 is an eight-position switch which is set by the physician to select one of the eight labelled rates. Another switch 24 is used to select both the mode of operation desired of the pacemaker and the pulse level. Label 22 indicates two possible modes, synchronous and asynchronous, and two possible pulse levels for each, the label thus identifying four of the eight positions of switch 24. Label 20 represents the third mode of operation, as well as the two pulse levels. (Two switch positions are provided for each of the high and low levels in the ventricular-inhibited mode simply because an eight-position switch may be used and there are only six combinations of mode/level values.)

When a program button (not shown) is depressed, the appropriate code transmission takes place, as will be described below. An audio tone is also heard in order that the physician be made aware that the programmer has operated. Indicator 14, labeled "Invalid", flashes whenever the program button is depressed in order to further inform the physician that the unit has operated. There are certain invalid combinations of parameters, namely, synchronous mode together with one of the three highest rates. (There are thus fewer than the 48 possible states discussed above.) In the event an invalid combination has been selected, indicator 14 does not flash and instead it remains illuminated to indicate that programming has not taken place. Indicator 12, labeled "Charge", is illuminated whenever the programmer is being charged. It flashes whenever re-charging is necessary.

The physician programmer can also be operated in a monitor mode by depressing a monitor button (not shown). If the coil pod is positioned near the electrode path, the stimulation rate, in pulses per minute, appears in window 16. Indicator 18 flashes whenever a pacemaker pulse is detected.

With two eight-position switches being provided, it is apparent that 64 different codes are possible. But because there are in actuality only six different mode/level combinations which can be set by switch 24, one-quarter of the 64 codes are interpreted by the pacemaker circuitry as representing the same respective states represented by another one-quarter of the codes; that is, although there are 64 codes, there are 16 pairs which represent the same respective states. The pacemaker circuitry must be capable, of course, of interpreting all 64 codes (except the invalid ones which are not transmitted). The actual transmission consists of eight "preamble" pulses, followed by anywhere from 0 to 63 additional pulses, the exact number of the additional pulses representing the code selected by the physician. The coding scheme will be described in detail below.

Figure 3:
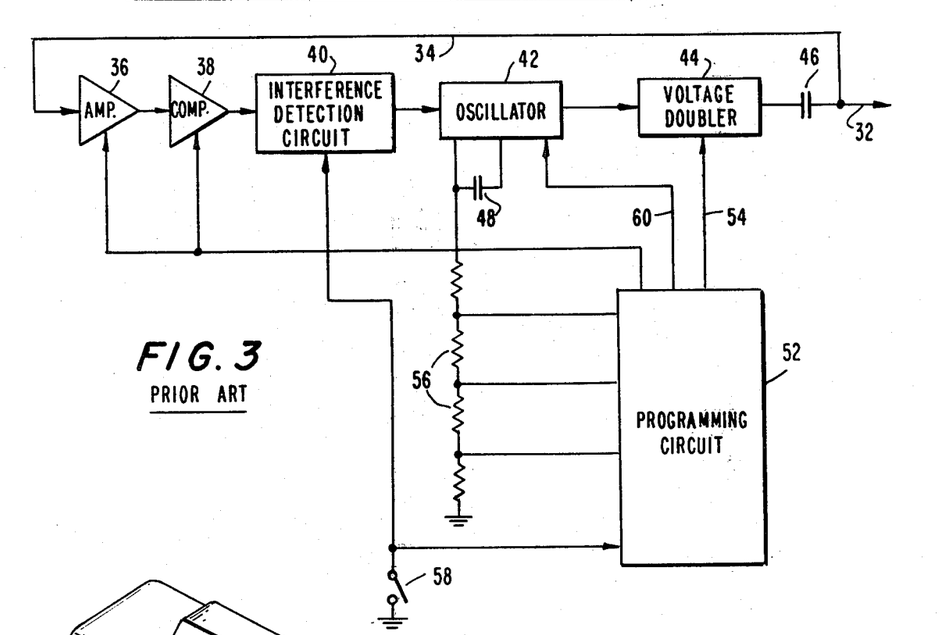
FIG. 3 depicts schematically a prior art programmable pacemaker, such as those marketed by Telectronics Proprietary Ltd.

FIG. 3 is a block diagram which depicts a typical programmable pacemaker. The basic timing circuit comprises oscillator 42, capacitor 48 and the four resistors 56. The programming circuit 52 is provided with three leads for selectively switching resistors 56 in and out of the circuit in order to control the rate of the oscillator, that is, in order to establish up to eight different discrete pacing rates. The output of the oscillator is extended to voltage doubler 44 whose operation is controlled by output 54 of the programming circuit. Depending on the state of this conductor, the voltage doubler applies either a 5.2-volt or a 2.6-volt pulse through capacitor 46 to electrode 32.

When the heart beats, the electrical signal on electrode 32 is extended over conductor 34 to the input of amplifier 36. As long as the system is operated in either the demand or the synchronous mode, conductor 50 is high in potential so that amplifier 36 and comparator 38 are enabled. The heartbeat signal is amplified and compared to a threshold level by comparator 38. The output of the comparator goes high whenever a heartbeat is detected. Interference detection circuit 40 simply blocks non-physiological signals which occur at high rates, as is known in the art, thus permitting oscillator 42 to run continuously. The oscillator operates either in the demand mode or the synchronous mode (either to prevent the generation of a stimulating pulse when a heartbeat is detected, or to reinforce it) depending upon the state of conductor 60 as determined by the programming circuit. Conductor 50 is low in potential when the pacemaker operates in the asynchronous mode, thereby inhibiting amplifier 36 and comparator 38 so that the oscillator is free running.

The electromagnetic pulses from a programmer operate reed switch 58. The switch pulses are extended to the programming circuit which, if a valid sequence is detected, changes the state of the pacemaker accordingly. The reed switch is also extended to the interference detection circuit in order to disable heartbeat sensing when the pacemaker is being programmed.

The programming circuit 52 verifies the code transmission and determines the state in which the pacemaker should be set. If at least eight (preamble) pulses are not detected, the programming circuit takes no action and ignores the transmission. Similarly, if more than the maximum number of 71 pulses (the eight preamble pulses plus the maximum number of 63 code pulses) are detected, the sequence is similarly aborted. Furthermore, each pulse must arrive between 2.5 milliseconds and 3.5 milliseconds after the previous pulse (the nominal pulse interval is 3 milliseconds), or else the transmission is assumed to be in error. Finally, after the last pulse within the proper ±0.5-millisecond window is detected, no additional pulses should be detected for 8 milliseconds. Only then does the programming circuit assume that the number of pulses received, less 8, represents a valid state code. The internal circuitry for accomplishing these checks need not be understood because the patient-operated programmer of our invention is designed to work with conventional pacemakers. But it is necessary to consider the form of the codes which the pacemaker expects to receive from the physician-operated programmer since the same codes must be transmitted by the patient-operated programmer.

Figure 4:
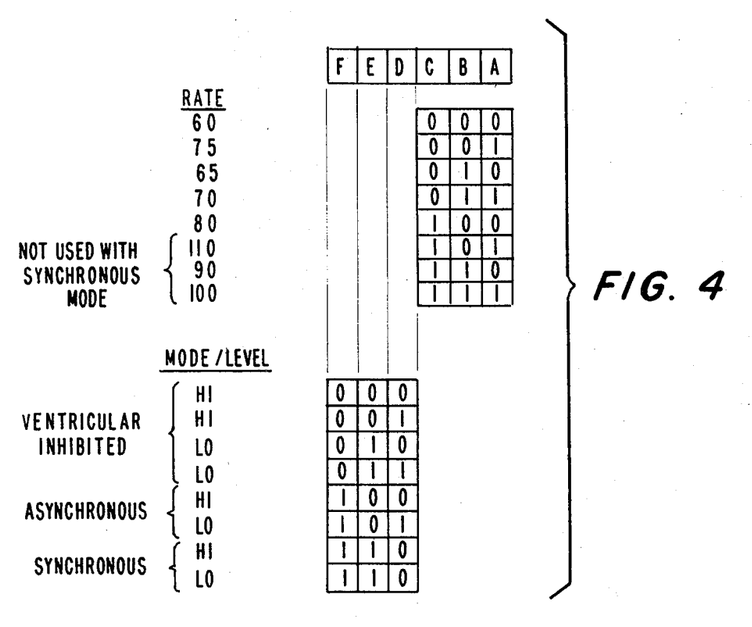
FIG. 4 is a chart which will be helpful in understanding the coding scheme used in the illustrative embodiment of the invention.

Forgetting for the moment the eight preamble pulses, FIG. 4 depicts the manner in which a binary code is established for controlling the transmission of anywhere from 0 to 63 pulses depending upon the settings of switches 24 and 26 on the physician programmer of FIG. 2. There are six binary positions with the most significant position being position A. The three least significant bits represent one of eight pulse rates. (As mentioned above, three of these rates should not be used with the synchronous mode.) The three most significant bits represent mode/level combinations. It will be noted that two of the eight possible codes represent a high pulse level in the ventricular-inhibited mode, and another two of the codes represent a low pulse level in the ventricular-inhibited mode. Thus there are really only six mode/level combinations, although there are eight different codes for representing them.

As a single example, consider the transmission of 51 pulses following the 8-pulse preamble. The decimal number 51 is represented by the binary number 110011. Referring to FIG. 4, if 59 (8+51) pulses are transmitted the pacemaker will begin to operate in the synchronous mode with a high pulse level (110) and at a rate of 70 beats per minute (011).

While the six-bit code of FIG. 4 represents numbers in the range 0-63, it is always necessary to transmit eight preamble pulses. If a binary number is used to represent the total number of pulses to be transmitted (anywhere from 8 to 71), seven bits are required to represent the number. In the illustrative embodiment of the invention, as will be described in detail below, three rate bits are used to set up the three least significant bits of a 7-bit binary number which represents the total number of pulses to be transmitted. But instead of using three bits to represent the eight mode/level combinations having binary codes 000 through 111, four bits are used for representing BCD codes (0000 through 1000) which correspond to the decimal digits 1-8. Because the mode/level code has its least significant bit in the fourth bit position of the overall code (which has a binary weight of $2^3$, or 8), the incrementing by unity of each mode/level code (from the range 000-111 to the range 0000-1000) actually results in an increase of 8 in the overall binary value.

Thus in order to represent the binary value of the total number of pulses to be transmitted, three rate bits may be used to set the three least significant bits of a seven-bit binary number, and four mode/level bits (representing BCD digits 1-8) may be used to set the four most significant bits of the seven-bit binary number. When the programming circuit in the pacemaker then ignores the first eight pulses which are received insofar as the transmitted code is concerned (although these pulses are used for verification purposes), the resulting number of received pulses will represent three parameter values as depicted on FIG. 4.

Figure 9:
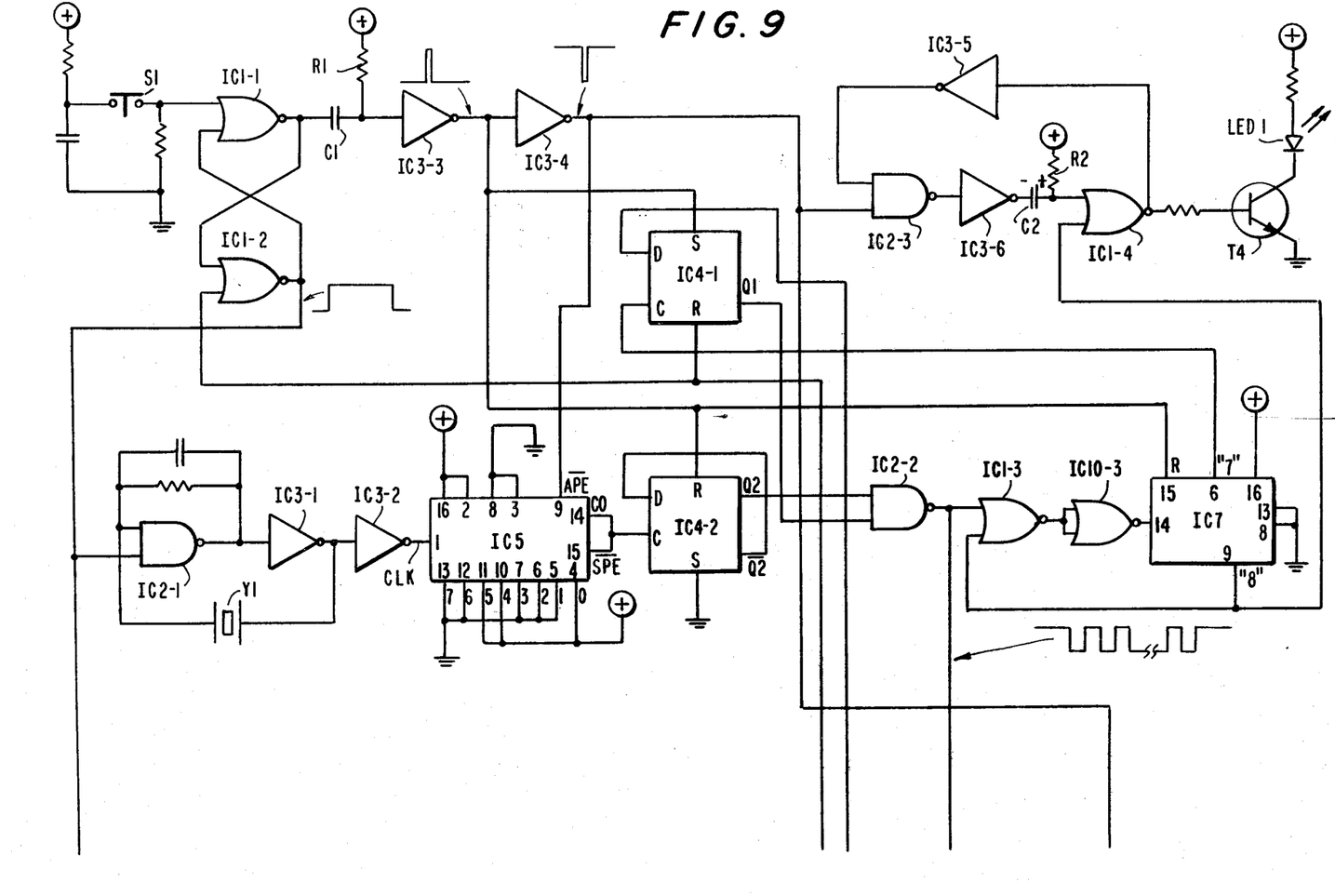
Figure 10:
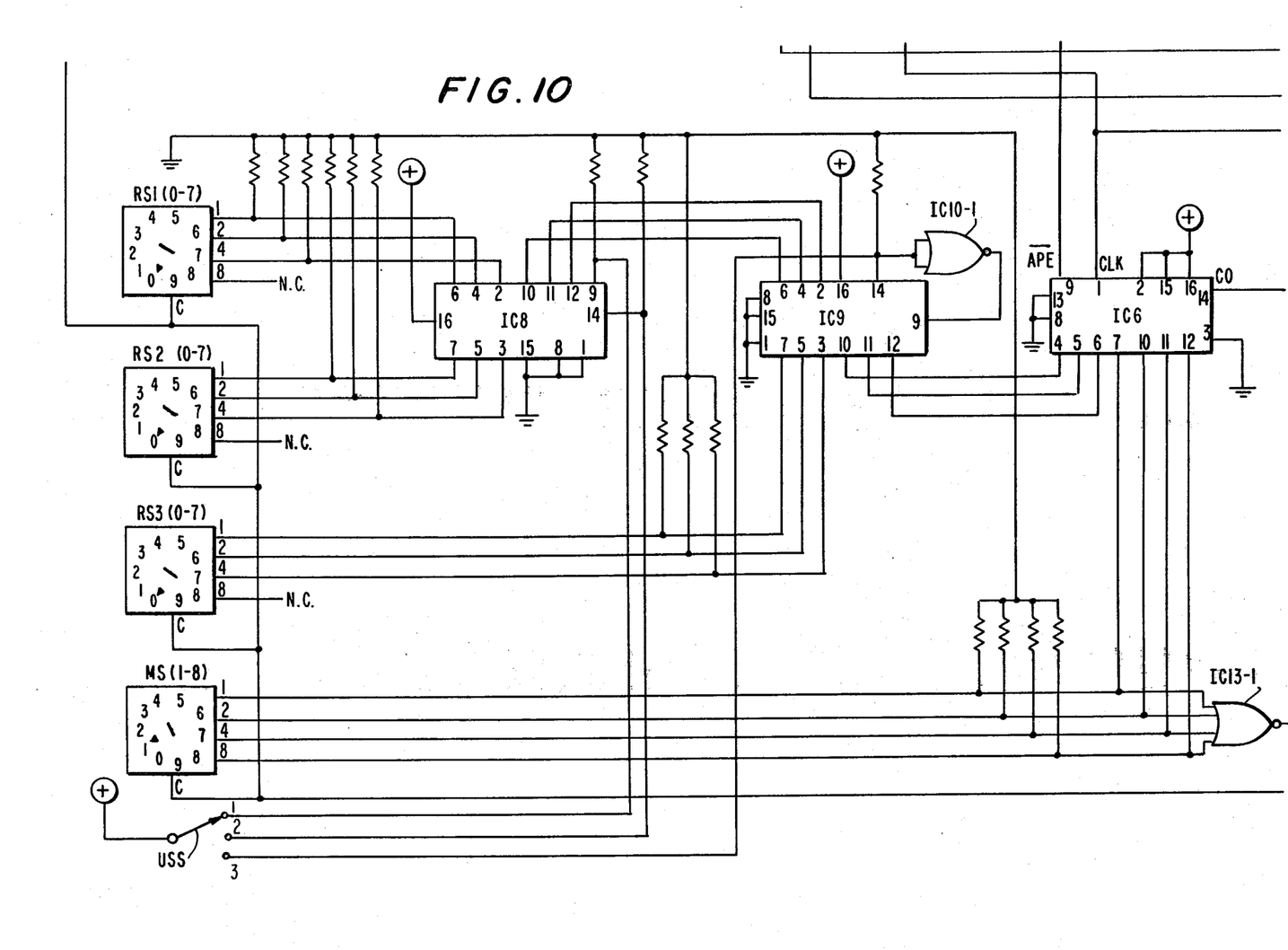
Figures 11, 12:
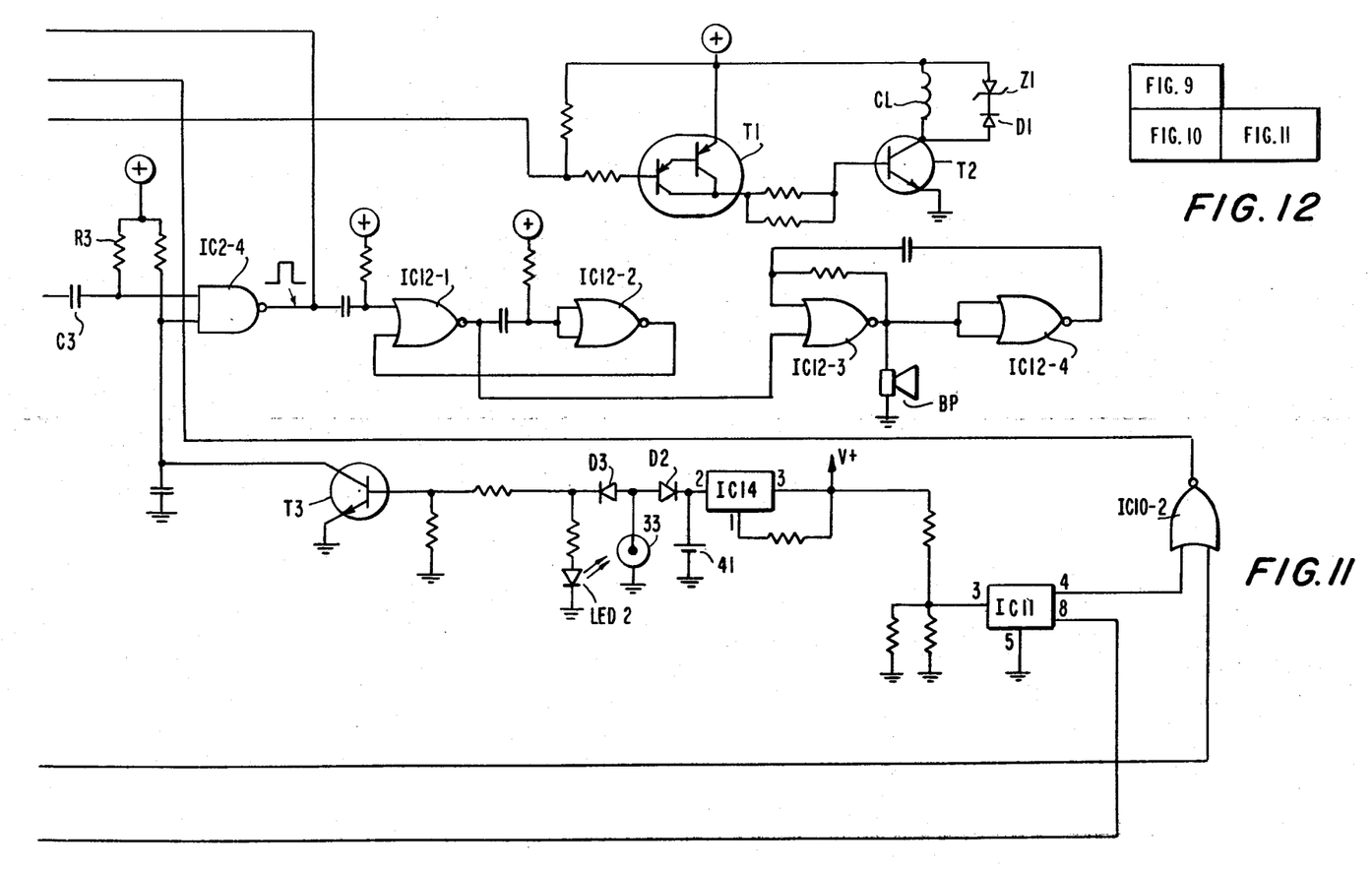

Referring to the schematic of the illustrative embodiment of the invention depicted in FIGS. 9-11, it is chip IC6 which is used to represent the 7-bit binary value. This chip is a 40103 8-stage pre-settable synchronous down counter. The counter is pre-set with an 8-bit number when the $\overline{APE}$ pin 9 is pulsed low. The eight bits which are pre-set are represented at pins 4–7 and 10–13. Pin 13 is tied to ground so that the most significant bit is always set to 0, since the maximum binary value to be pre-set corresponds to the number 71. The mode/level bits are applied to pins 7 and 10–12. As described above, the four mode/level bits represent the BCD digits 1–8 for the respective binary codes 000 through 111 shown on FIG. 4, to insure that eight preamble pulses are always transmitted in addition to the number of code pulses actually required.

As clock pulses are applied to pin 1, the count is decremented. When the count has been decremented down to 0, a positive pulse is generated at pin 14. As will be described, the CO pulse causes pulsing of the coil to cease, and thus it is apparent that the number of code pulses generated depends upon the three rate bits and the four mode/level bits pre-set into the counter.

On FIG. 10 there are four BCD switches (Micro-Dip 2300 Series) which are pre-set by the physician. Switch RS1 is set to one of the values 0–7 to represent the "sleep" pulse rate desired by the physician. A positive potential applied to the C input of the switch results in positive potentials on appropriate ones of the "1", "2" and "4" outputs, the remaining outputs being grounded through their respective pull-up resistors. The binary value thus represented corresponds to the decimal value selected by the physician. (There is no connection to the "8" output since it is not required; only three bits are required to represent the digits 0–7.)

In a similar manner, switch RS2 is used by the physician to set the "awake" pulse rate, and switch RS3 is used to set the "exercise" pulse rate. Switch MS is used by the physician to set the mode and level parameter values. The physician must select one of the digits 1–8 (corresponding to the codes 000–111 on FIG. 4). But in this case all four outputs of the switch are required since the BCD digit 8 is represented by the binary code 1000.

The four physician-settable switches are not accessible to the patient (unless he deliberately unscrews the plate which covers them). The only switch which is operated by the patient is the user select switch USS. If the patient selects position 1 (labeled "sleep" on the housing of the programmer), the BCD code of switch RS1 is loaded into the three least significant bit positions of counter IC6. Similarly, if he selects position 2 or 3 (the "awake" and "exercise" positions), the respective digits represented by switch RS2 or RS3 are loaded into the three least significant bit positions of counter IC6. Thus the patient cannot select from among all eight possible rates to which the pacemaker can be set. The patient's selection is limited to three rates pre-selected by the physician. (The patient need not even know what the rate values are since his selection is based upon his activity.)

As for the mode and level parameters, in the illustrative embodiment of the invention they are not under control of the patient at all. His switch USS has no control over the loading of the four most significant bits of the 7-bit binary value pre-set in chip IC6 since the outputs of switch MS are coupled directly to respective pins on chip IC6. Although a patient programmer can be designed to allow the patient to select mode and level parameter values from a sub-set selected by the physician (certainly, in the case of the level parameter, the patient's sub-set of values would be congruent with the physician's set of values since there are only two values), that is not the case in the illustrative embodiment of the invention. It should be noted, however, that it is still necessary to transmit a code which represents not only the value of the parameter under control of the patient, but the values of all parameters. The pacemaker responds to the total number of pulses, and this total number represents values for all three parameters; even if only one parameter value is to be changed, a complete code must be transmitted. It is for this reason that mode switch MS is included in the circuit.

Chips IC8 and IC9 control which of the three rate codes is loaded into the three least significant positions of counter IC6. Each of chips IC8 and IC9 is a 4519 Quad 2-channel data selector. Pins 2, 4, 6 and 15 comprise one input channel, and pins 1, 3, 5 and 7 comprise the other. Pins 1 and 15 are grounded on each chip since each code input consists of only three bits. The outputs of switches RS1 and RS2 are connected to respective ones of the two sets of inputs on chip IC8. The four input bits of the chip appear at pins 10–13, but no connection is made to pin 13 since each of the inputs consists of only three bits. Which of the two sets of inputs are extended to the outputs are determined by the states of pins 9 and 14.

If switches USS is at position 3, both of pins 9 and 14 on chip IC8 remain grounded through their respective pull-up resistors. Neither set of inputs is selected and pins 10, 11 and 12 are all low. The states of these pins is of no moment, however. They are connected to pins 2, 4 and 6 of selector IC9. But with switch USS connected to position 3, a high potential is applied to pin 14 of chip IC9 and, through NOR (inverter) gate IC10-1, a low potential is applied to pin 9. With a high potential at pin 14 and a low potential at pin 9, the signals at pins 3, 5 and 7 of chip IC9 are extended to output pins 10, 11 and 12. Since pins 3, 5 and 7 are connected to the outputs of "exercise" switch RS3, it is apparent that the "exercise" rate code bits are extended to pins 4, 5 and 6 of counter IC6.

On the other hand, if switch USS is set by the patient to either the "sleep" or the "awake" position, pin 14 on chip IC9 is grounded through its pull-up resistor, and NOR gate IC10-1 causes pin 9 to go high. In such a case, the bit vaues at pins 2, 4 and 6 of chip IC9 are extended to the output pins 10, 11 and 12 for loading into the counter. Thus it is the bit outputs from chip IC8 which are extended through chip IC9 to be loaded into the counter when switch USS is placed in position 1 or 2.

If it is placed in position 1, a positive potential is extended through the switch to pin 9 of chip IC8, and pin 14 remains grounded through its pull-up resistor. In such a case, the code bits from switch RS1 are loaded into the counter. On the other hand, if switch USS is placed in position 2, a positive potential is applied to pin 14 of chip IC8, and pin 9 remains grounded through its pull-up resistor. In such a case, it is the code bits at the output of switch RS2 which are loaded into the three rate bit positions of counter IC6.

Referring to FIG. 9, after the patient selects the "sleep", "awake" or "exercise" function, he operates switch S1. Gates IC1-1 and IC1-2 comrpise a latch, and operation of switch S1 causes the output of gate IC1-1 to go low and the output of gate IC1-2 to go high. It is the high potential at the output of gate IC1-2 which allows counter IC6 to be set in the first place (along with the negative pulse from gate IC3-4 which is applied to the $\overline{APE}$ pin 9 of the chip), since it is this potential which is extended to the C input of each of the four switches RS1–RS3 and MS. The high potential is also extended to an input of gate IC2-1. This gate, together with inverter IC3-1 and crystal Y1, comprise an oscillator. After inversion by chip IC3-2, clock pulses are applied to the clock input of chip IC5. This chip is also a 40103 pre-settable synchronous down counter. Its eight inputs are tied respectively to ground and battery potentials as shown, for loading of a count of 49 into the counter. Resistor R1 and capacitor C1 comprise a differentiator, and inverters IC3-3 and IC3-4 derive positive and negative pulses respectively as shown in the drawing. The negative pulse at the output of inverter IC3-4 is applied to the $\overline{APE}$ pin 9 of chip IC5 to load the counter to a value of 49. Because the C0 output pin 14 is tied to the $\overline{SPE}$ input pin 15 of chip IC5, whenever the count is counted down to 0, it is pre-set once again with a count of 49. (This is to distinguished from the configuration of chip IC6 whose count is not pre-set once again after it is counted down to 0 since the C0 pin is not tied back to the $\overline{SPE}$ pin.) Crystal Y1 controls the oscillator to oscillate at a rate of 32,768 kHz. Because chip IC5 functions as a divide-by-49 counter, pulses are applied to the clock input of flip-flop IC4-2 at a 668-Hz rate. The flip-flop is arranged as a divide-by-2 counter because its Q2 output is fed back to its D input. Thus clock pulses are applied at the $\overline{Q2}$ output of the flip-flop at a 334-Hz rate. This is the basic clock signal which drives down counter IC6 as well as additional circuitry to be described.

Chip IC7 is a 4017 decade counter/divider. It is initially reset (at pin 15) by the positive start pulse at the output of gate IC3-3. This same pulse resets flip-flop IC4-2 whose Q2 output goes low, and sets flip-flop IC4-1 whose Q1 output goes high. With the Q1 output of flip-flop IC4-1 high, one input of gate IC2-2 is enabled. Each time that the Q2 output of flip-flop IC4-2 goes high, the output of gate IC2-2 goes low. It is the negative pulses at the output of this gate that actually control drive of the coil, as will be described below, and decrementing of the count in chip IC6.

Pins 6 and 9 of chip IC7 are initially low in potential. Pin 6 goes high when the leading edge of the seventh positive pulse is applied to clock pin 14. It goes low when the leading edge of the eighth positive pulse is applied to the clock input, at which time pin 9 goes high. Since initially pin 9 is low in potential, it has no effect on NOR gate IC1-3. But each time that the output of gate IC2-2 goes high, the output of gate IC1-3 goes low, and gate IC10-3, which functions as an inverter, clocks chip IC7. It is thus apparent that at the trailing edge of the seventh negative pulse at the output of gate IC2-2, pin 6 of chip IC7 goes high. This pin is connected to the clock input of flip-flop IC4-1. Provided that the D input of the flip-flop is high, the Q1 output remains high so that the next clock pulse can be transmitted through gate IC2-2. (As will be described below, the pulse at pin 6 of chip IC7 is used to switch flip-flop IC4-1 to the 0 state with the Q1 output going low so as to inhibit the further transmission of pulses, in the event the battery potential is too low by the time the seventh pulse has been transmitted—in which case the pacemaker ignores the seven pulses generated, assuming that they were received, since the programmer reliability is in doubt.) After the eighth positive step is applied to pin 14 of chip IC7, output pin 9 goes high. A positive potential is now extended through gates IC1-3 and IC10-3 to the pin 14 clock input of chip IC7. With a positive potential remaining on this pin, it no longer cycles and pin 9 remains high. Although clock pulses may still be generated by chip IC2-2 (unless the required code calls for no pulses after the preamble), they are used only to control the continuation of pulse transmission.

Gates IC2-3, IC3-6, IC1-4 and IC3-5 comprise a monostable multivibrator with a period of twenty seconds. The multivibrator is triggered by the initial negative pulse at the output of inverter IC3-4. One input of gate IC1-4 is connected to pin 9 of chip IC7, and initially this pin is low in potential. Consequently, when the output of inverter IC3-6 goes low with the generation of a negative pulse at the output of inverter IC3-4, the output of gate IC1-4 goes high, transistor T4 conducts and light-emitting diode LED1 is turned on. If the battery potential is high enough for reliable operation to be assumed, after the eighth pulse has been transmitted pin 9 of chip IC7 goes high and remains high. The high potential now extended through gate IC1-4 causes its output to remain low and consequently transistor T4 turns off. Thus if the battery potential is high enough, light-emitting diode LED1 stays on only for the duration of eight pulses, each of which takes about 3 milliseconds. The short flash is an indication to the patient that his programmer has operated. On the other hand, if the battery potential is too low, when pin 6 of chip IC7 goes high after the seventh pulse has been transmitted, the D input of flip-flop IC4-1 is low, as will be described below. When the Q1 output of the flip-flop goes low, no further pulses are transmitted through gate IC2-2, and pin 9 of chip IC7 is not clocked high. Consequently, the multivibrator is allowed to complete its time-out, and the 20-second turn-on of the light emitting diode is an indication to the patient that his pacemaker has not been programmed and that the battery requires re-charging.

The pulses appearing at the output of gate IC2-2 are applied to the clock input of chip IC6. Pulse transmission must cease after the number of pulses transmitted equals the count initially pre-set in chip IC6. After the counter has been decremented down to 0, a pulse appears on the C0 output pin 14 of chip IC6. The leading edge of the positive pulse has no effect on gate IC2-4 since both of its inputs are connected to battery potential. However, due to the provision of differentiator R3-C3, the trailing edge of the pulse causes a low potential to be applied to one input of gate IC2-4. (The gate must not be operated until the end of the last pulse which is transmitted, and consequently the differentiator is provided to ensure that it is the trailing edge of the last pulse which turns everything off.) The output of gate IC2-4 goes high and since it is extended to the reset input of flip-flop IC4-1, the Q1 output of the flip-flop goes low. No further pulses are transmitted through gate IC2-2 so pulse transmission ceases. The same reset pulse is also applied to the latch which comprises gates IC1-1 and IC1-2, so that it is restored to its normal condition with the output of gate IC1-2 low; this turns off the oscillator and restores the circuit to its quiescent condition.

The same positive pulse at the output of gate IC2-4 triggers the 200-millisecond multivibrator which comprises chips IC12-1 and IC12-2. The negative pulse at the output of gate IC12-1 turns on the 2-kHz oscillator which comprises chips IC12-3 and IC12-4. Thus for 200 milliseconds, the oscillator operates and causes beeper BP to beep. The momentary beep is a further indication of the patient that his programmer has operated.

The pulse train at the output of gate IC2-2, in addition to decrementing the count is chip IC6, is also extended to the input of Darlington transistor T1. Each negative pulse causes the transistor to conduct and to drive transistor T2. It is this transistor which actually pulses coil CL to control the transmission of pulses to the pacemaker. Diode D1 is provided in order to allow the current in the coil to dissipate between pulses when transistor T2 turns off. Zener diode Z1 insures that the energy completely dissipates during the approximately 1.5-millisecond off time of transistor T2.

The battery for powering the programmer is shown by the numeral 41 on FIG. 11. Chip IC14 is a current source arranged to provide a regulated voltage V+ for powering all of the logic elements. Chip IC11 is an ICL8212 chip arranged to detect if the battery potential (which is nominally 7.2 volts) falls so low that the potential V+ drops below 6.6 volts. (One of the two grounded resistors at pin 3 has a value which is selected by testing each unit, to insure that all units have the same threshold). Chip IC11 is enabled by a high potential at its pin 8, and it will be noted that this pin is connected to the output of chip IC1-2 which goes high when the patient first operates the start switch. As long as potential V+ remains above 6.6 volts, pin 4 of chip IC11 remains low and the output of gate IC10-2 remains high. Since this output is connected to the D input of flip-flop IC4-1, it is apparent that after the seventh pulse has been transmitted, the Q1 output of the flip-flop will go low only if the battery potential is too low for reliable operation to be assumed. (Flip-flop IC4-1 is clocked only after the seventh pulse has been transmitted in order to delay the battery test; while the battery potential may be high enough initially, if the battery requires re-charging its potential will usually fall below 6.6 volts by the time the seventh pulse has been transmitted).

It should also be noted that there is another input to gate IC10-2. This input is derived from the output of gate IC13-1. It will be recalled that the mode switch MS must be set by the physician in only one of positions 1-8. If he erroneously selected position 0, all four outputs of switch MS will be low and only in this case will the output of gate IC13-1 be high. This high potential is treated as if a low battery indication had been detected, to prevent transmission of an erroneous code.

It will be recalled that the system is reset when chip IC6 generates a pulse at pin 14 after its count has been decremented down to 0. But if the battery potential is too low, gate IC2-2 turns off after the seventh pulse has been transmitted, and clock pulses are no longer applied to pin 1 of chip IC6. Thus a reset pulse cannot be generated in the usual way, and the latch remains in its set state with the output of chip IC1-1 low. Consequently, further operations of the start button S1 by the patient have no effect on the system. The only way to reset the programmer so that it can be used again is to connect a charging circuit to jack 33. The positive potential applied to the base of transistor T3 causes the transistor to turn on and the output of gate IC2-4 to go high. Although the latch resets, as long as the charger remains connected to the circuit, the programmer cannot be operated because the output of gate IC2-4 remains high and this output is connected to the reset input of flip-flop IC4-1; the Q1 output of the flip-flop remains low so that gate IC2-2 cannot be pulsed. Operation of start button S1 does force the output of gate IC1-1 to go low for as long as the start button is depressed. (The high potential at the output of gate IC2-4 holds the output of gate IC1-2 low also). The pulse at the output of gate IC1-1 triggers the 20-second multivibrator so that light-emitting diode LED1 remains on continuously for twenty seconds to inform the patient that programming has not taken place.

The additional light-emitting diode LED2 is provided simply to indicate that charging is taking place, the diode staying on for as long as a charging circuit is connected to jack 33. Diodes D2 and D3 are provided to prevent any damage to chip IC14, transistor T3 and light-emitting diode LED1 in the event a reverse polarity charger is connected to jack 33.

Figure 5:
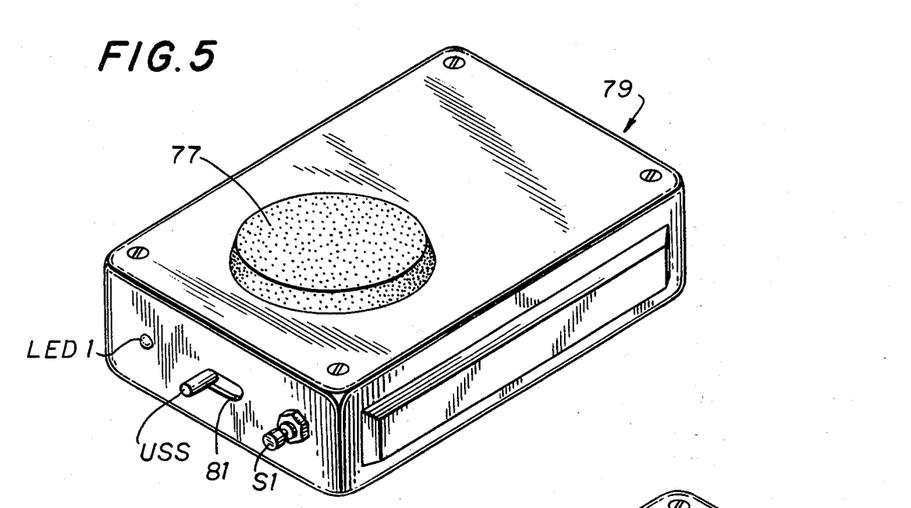
FIGS. 5-7 depict several views of the patient-operated pacemaker programmer of the illustrative embodiment of our invention.
Figures 6, 7:
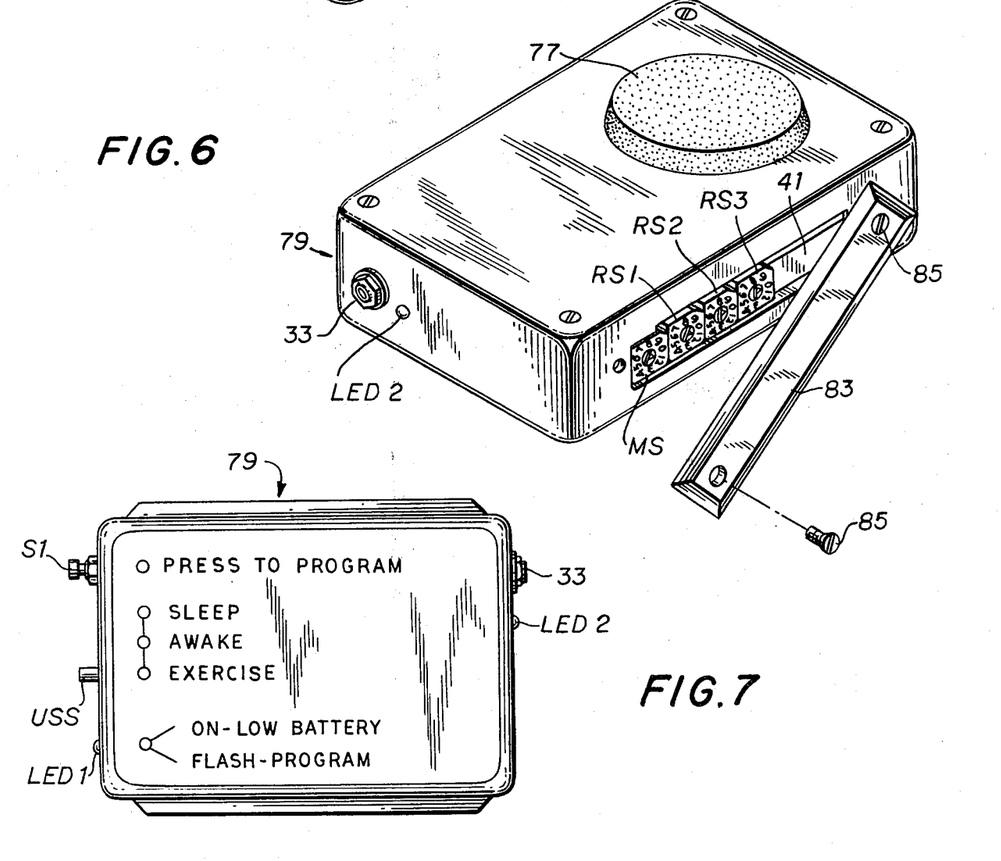

FIGS. 5 and 6 are perspective views of the patient-operated programmer, and FIG. 7 depicts the bottom of the device. On housing 79, plastic sheet 77 covers the coil which generates the pulses. At one end of the device, user select switch USS can be moved within cut-out 8, start switch S1 can be operated, and light-emitting diode LED1 can be viewed.

On the non-coil side of the programmer, as shown in FIG. 7, there is printed user information. Next to the start switch S1 is the "press to program" instruction. Before switch S1 is operated, the patient moves slide switch USS to one of the three indicated positions—"sleep", "awake" and "exercise". Next to light-emitting diode LED1 are the two status indicator codes. If the light stays on continuously, it is an indication that the battery potential is too low. But if the light flashes, it is an indication that the coil has been pulsed as required.

FIG. 6 shows the charging jack 33 and the associated light-emitting diode LED2. It also depicts how cover plate 83, which is normally held by two screws 85, can be rotated so as to gain access to the four switches MS, RS1, RS2 and RS3. Battery 41 is also disposed adjacent to plate 83 so that the battery may be changed easily, if that is necessary. As described above, the patient is instructed not to open cover plate 83; it is only the physician who is to have access to the four switches.

Figure 8:
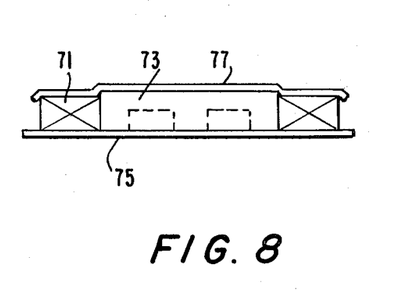
FIG. 8 is a cross-sectional view through the coil included in the patient programmer of FIGS. 5-7.

FIG. 8 depicts the construction of the coil section of the programmer. The coil, depicted by the numeral 71, comprises 100 turns wound around a 45-mm pot core 73. The core has a height of 10 mm. Ordinarily, two such facing cores are used together in transformer construction, with the coil being partially contained in each core within the cut-out shown by the dashed lines. But in the illustrative embodiment of the invention, the coil is actually wound around the outside of the core. The entire assembly is mounted on a transformer steel plate 75, and the core and the coil are covered with plastic sheet 77, the sheet being part of the case which houses the patient-operated programmer circuitry.

Figure 13:
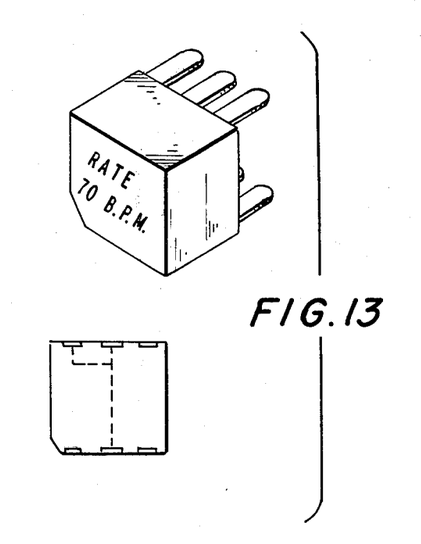
FIG. 13 depicts an alternative form of switch which can be used in the patient programmer to allow the physician to pre-select parameter values.

In the illustrative embodiment of the invention, four physician-operated switches are provided for maximum flexibility. However, instead of providing switches of this type, it is also possible to provide molded pre-wired plug-in elements for selecting mode/level and rate parameter values. FIG. 13 depicts such a plug-in element. The unit includes six pins so that it can physically replace one of the switches. The pins are internally wired to provide the same BCD output code that would otherwise be obtained by having the physician rotate a switch to the desired position. Each plug-in element is actually labelled (70 beats per minute in the illustrated example) with a parameter value to minimize the possibility of a mistake when selecting an element. The physician must be furnished with a full set of parameter-value elements which may be inserted into the programmer instead of the unit coming with multi-value switches. But there is no risk of the patient tampering with switch settings. Preferably, the plug-in elements are polarized as shown in the drawing (i.e., non-symmetrical) so that there is no chance of inserting an element with an improper orientation.

In the illustrative embodiment of the invention, the following elements are used for the indicated components:

| IC1 | 4001 | IC13 | 4002 |
|-----|------|------|------|
| IC2 | 4011 | IC14 | LM324 |
| IC3 | 4069 | T1 | TIP117 |
| IC4 | 4013 | T2 | BD437 |
| IC5 | 40103 | T3 | BC549 |
| IC6 | 40103 | T4 | BC549 |
| IC7 | 4017 | D1 | A14A |
| IC8 | 4519 | D2, D3 | 1N914 |
| IC9 | 4519 | LED1 | HP5082-4684 |
| IC10 | 4001 | LED2 | HP5082-4684 |
| IC11 | ICL8212 | Z1 | 1N5346 |
| IC12 | 4001 | BP | Murata PKM11-4A0 |

It should be understood, however, that these are only illustrative components. Moreover, instead of using discrete logic, it is possible to utilize a custom LSI chip or a microprocessor for controlling all logic functions. Nor is the invention limited to the particular parameters or parameter values discussed above. For example, certain arrhythmias (e.g., multifocal ventricular extrasystoles) are self-detectable, and a patient-operated programmer may be operable to set a rate which terminates an arrhythmia; the unit would include an "arrhythmia terminator" patient-operated switch position and a respective physician-settable rate switch. It is also possible to provide monitoring circuits in the patient programmer so that following a programming operation, the patient might use his unit to check that his pacemaker has actually been programmed correctly. Thus it is to be understood that although the invention has been described with reference to a particular embodiment, this embodiment is merely illustrative of the application of the principles of the invention. Numerous modifications may be made therein and other arrangements may be devised without departing from the spirit and scope of the invention.

What we claim is:

1. A programming system for a pacemaker, said pacemaker having at least one parameter characteristic of its operation whose value can be changed by an external programming source, said parameter being changeable to any one of a predetermined number of discrete values, comprising:
   a physician-operated programmer for transmitting signals to said pacemaker, having manually adjustable means for controlling the changing of said parameter to any selected value of said predetermined number of discrete values; and
   a patient-operated programmer for transmitting signals to said pacemaker, having manually adjustable means for controlling the changing of said parameter to any selected value of a group, smaller than said predetermined number, of discrete values,
   whereby a patient can control his pacemaker to change to a state selected from a sub-set of the set of states under control of the physician,
   said patient-operated programmer including means, normally under control of a physician, for pre-selecting those parameter values in said predetermined number of discrete values which are included in said group, whereby a physician can pre-select those states in the set under his control which are included in the sub-set under control of the patient.

2. A pacemaker programming system in accordance with claim 1 wherein said parameter is pacing rate.

3. A pacemaker programming system in accordance with claim 1 wherein said manually adjustable means in said patient-operated programmer has a group of indicia associated therewith which, instead of representing respective discrete parameter values, represent day-to-day physiological requirements of the patient.

4. A pacemaker programming system in accordance with claim 1 wherein said manually adjustable means in said patient-operated programmer has a group of indicia associated therewith which, instead of representing respective discrete parameter values, represent day-to-day physiological requirements of the patient.

5. A pacemaker programming system in accordance with claim 1 wherein said patient-operated programmer further includes means for providing a verifying indication to said patient that signals have been transmitted.

6. A programming system for a pacemaker, said pacemaker having at least two parameters characteristic of its operation whose values can be changed by an external programming source, each of said parameters being changeable to respective discrete values, comprising:
   a physician-operated programmer for transmitting signals to said pacemaker, having manually adjustable means for controlling the changing of each of said parameters to a selected one of the respective discrete values; and
   a patient-operated programmer for transmitting signals to said pacemaker for controlling the changing of less than all of said pacemakers, having manually adjustable means for controlling the changing of each changeable parameter to a selectable one of the respective discrete values,
   whereby a patient can control his pacemaker to change to a state selected from a sub-set of the set of states under control of the physician,
   said patient-operated programmer including means, normally under the control of a physician, for selecting those states in the set under his control which are included in the subset under control of the patient, said patient-operated programmer including means, normally under control of a physician, for selecting those states in the set under his control which are included in the subset under control of the patient.

7. A pacemaker programming system in accordance with claim 6 wherein said parameters include at least pacing rate and mode of operation, and said patient-operated programmer transmits signals for changing the pacemaker rate but not the pacemaker mode of operation.

8. A pacemaker programming system in accordance with claim 7 wherein said physician-operated programmer can control the changing of pacemaker rate to any value of a predetermined number of values, and said patient-operated programmer can control the changing of pacemaker rate to less than all of said predetermined number of values.

9. A pacemaker programming system in accordance with claim 8 wherein said means in said patient-operated programmer, normally under the control of the physician, allows the physician to preselect those pacemaker rates which can be controlled by said patient programmer.

10. A pacemaker programming system in accordance with claim 6 wherein said manually adjustable means in said patient-operated programmer has a group of indicia associated therewith which, instead of representing respective discrete parameter values, represent day-to-day physiological requirements of the patient.

11. A pacemaker programming system in accordance with claim 6 wherein said patient-operated programmer further includes means for providing a verifying indication to said patient that signals have been transmitted.

12. A programming system for a pacemaker, said pacemaker having at least two parameters characteristic of its operation whose values can be changed by an external programming source, each of said parameters being changeable to any one of a predetermined number of respective discrete values, comprising:
  a physician-operated programmer for transmitting signals to said pacemaker, having manually adjustable means for controlling the changing of each of said parameters to any selected value of said predetermined number of respective discrete values; and
  a patient-operated progammer for transmitting signals to said pacemaker for controlling the changing of less than all of said parameters, having manually adjustable means for controlling the changing of each changeable parameter to any selected value of a respective group, smaller than said respective predetermined number, of discrete values,
  whereby a patient can control his pacemaker to change to a state selected from a sub-set of the set of states under control of the physician,
  said patient operated programmer including means, normally under the control of a physician, for pre-selecting for each changeable parameter those values in said pre-determined number of respective discrete values which are included in said respective group, whereby a physician can pre-select those states in the set under his control which are included in the sub-set under control of the patient.

13. A pacemaker programming system in accordance with claim 10 wherein pacing rate is a patient-operated programmer changeable parameter.

14. A pacemaker programming system in accordance with claim 12 wherein said manually adjustable means in said patient-operated programmer has a group of indicia associated therewith which, instead of representing respective discrete parameter values, represent day-to-day physiological requirements of the patient.

15. A pacemaker programming system in accordance with claim 12 wherein said patient-operated programmer further includes means for providing a verifying indication to said patient that signals have been transmitted.

16. A programming system for a pacemaker, said pacemaker having at least two parameters characteristic of its operation whose values can be changed by an external programming source, each of said parameters being changeable to respective associated values, comprising:
  a physician-operated programmer for transmitting signals to said pacemaker, having manually adjustable means for controlling the changing of each of said parameters to any of the respective associated values; and
  a patient-operated programmer for transmitting signals to said pacemaker for controlling the changing of less than all of said parameters, having manually adjustable means for controlling the changing of each changeable parameter to less than all of the respective associated values,
  said patient-operated programmer including means, normally under the control of a physician, for pre-selecting for each changeable parameter those of the respective associated values which can be changed by the patient-operated programmer.

17. A pacemaker programming system in accordance with claim 16 wherein pacing rate is a patient-operated programmer changeable parameter.

18. A pacemaker programming system in accordance with claim 16 wherein said manually adjustable means in said patient-operated programmer has a group of indicia associated therewith which, instead of representing respective parameter values, represent day-to-day physiological requirements of the patient.

19. A pacemaker programmer intended for patient use, said pacemaker having a plurality of states characteristic of its operation, the pacemaker being changeable to any of said plurality of states by an external programming source, comprising means for transmitting signals to said pacemaker to control a change of state; manually adjustable means, normally under the control of a patient, for selecting a pacemaker state from a group consisting of less than all of said plurality of states and controlling the transmission of a corresponding signal; and means, normally under the control of a physician, for pre-selecting those states in said group whereby a physician can pre-select those states from said plurality of states which are included in the group selectable by the patient.

20. A pacemaker programmer in accordance with claim 19 wherein all of said plurality of pacemaker states differ from each other by up to a number of parameters, one of which is pacemaker rate, and the states in said group differ from each other by up to only a lesser number of parameters.

21. A pacemaker programmer in accordance with claim 20 wherein said lesser number of parameters includes only pacemaker rate.

22. A pacemaker programmer in accordance with claim 19 wherein each of said plurality of pacemaker states is characterized by the value of at least one parameter, said at least one parameter having a predetermined number of discrete values, and all pacemaker states in said group are characterized by said at least one parameter having a number of discrete values which is less than said predetermined number.

23. A pacemaker programmer in accordance with claim 22 wherein said at least one parameter is pacemaker rate.

* * * * *